United States Patent
Houjou et al.

(10) Patent No.: US 9,595,084 B2
(45) Date of Patent: Mar. 14, 2017

(54) MEDICAL SKIN EXAMINATION DEVICE AND METHOD FOR ENHANCING AND DISPLAYING LESION IN PHOTOGRAPHED IMAGE

(71) Applicant: CASIO COMPUTER CO., LTD., Tokyo (JP)

(72) Inventors: Yoshiharu Houjou, Nerima Tokyo (JP); Nobuhiro Aoki, Kokubunji Tokyo (JP)

(73) Assignee: CASIO COMPUTER CO., LTD. (JP)

( * ) Notice: Subject to any disclaimer, the term of this patent is extended or adjusted under 35 U.S.C. 154(b) by 0 days.

(21) Appl. No.: 14/613,084

(22) Filed: Feb. 3, 2015

(65) Prior Publication Data

US 2015/0221087 A1    Aug. 6, 2015

(30) Foreign Application Priority Data

Feb. 5, 2014    (JP) .................................. 2014-019906

(51) Int. Cl.
   *G06K 9/00*        (2006.01)
   *G06T 5/00*        (2006.01)
   (Continued)

(52) U.S. Cl.
   CPC ............ *G06T 5/009* (2013.01); *A61B 5/0077* (2013.01); *A61B 5/444* (2013.01); *G06T 5/50* (2013.01);
   (Continued)

(58) Field of Classification Search
   None
   See application file for complete search history.

(56) References Cited

U.S. PATENT DOCUMENTS

| 7,689,016 B2 * | 3/2010 | Stoecker | G06F 19/321 |
| | | | 382/128 |
| 2012/0027076 A1 * | 2/2012 | Su | G06T 5/007 |
| | | | 375/240.02 |
| 2015/0221087 A1 * | 8/2015 | Houjou | G06T 5/50 |
| | | | 382/128 |

FOREIGN PATENT DOCUMENTS

| JP | 2005-192944 A | 7/2005 |
| JP | 2007-152084 A | 6/2007 |

(Continued)

OTHER PUBLICATIONS

Sato et al. ("Improved Detection of Dermoscopic Structures by High Dynamic Range Image Conversion"; Japanese Journal of Dermatology; vol. 123, No. 2, pp. I21 -131; Feb. 2013 and English abstract of the same (12 pages), hereby referred to as "Sato"). Obtained via STIC department for translation.*

(Continued)

*Primary Examiner* — Tahmina Ansari
(74) *Attorney, Agent, or Firm* — Fitch Even Tabin & Flannery LLP

(57) ABSTRACT

A medical skin examination device configured to diagnose a skin lesion includes: a first storage unit configured to store an original first skin image related to a dermoscopy structure imaged via a dermoscope; an image conversion unit configured to apply High Dynamic Range (HDR) conversion processing to the first skin image and obtain a second skin image in which the dermoscopy structure is made clear and salient; a second storage unit configured to store the second skin image; and a display control unit configured execute control so as to display at least one of the first skin image and the second skin image.

15 Claims, 9 Drawing Sheets

(51) Int. Cl.
   *G06T 5/50*     (2006.01)
   *A61B 5/00*    (2006.01)
(52) U.S. Cl.
   CPC ............... *G06T 2207/10024* (2013.01); *G06T 2207/10144* (2013.01); *G06T 2207/20016* (2013.01); *G06T 2207/20208* (2013.01); *G06T 2207/20212* (2013.01); *G06T 2207/30088* (2013.01); *G06T 2207/30096* (2013.01)

(56) References Cited

FOREIGN PATENT DOCUMENTS

| JP | 2008-250750 A | 10/2008 |
| JP | 2011-24885 A | 2/2011 |
| JP | 2012-213555 A | 11/2012 |

OTHER PUBLICATIONS

"Improved Detection of Dermoscopic Structures by High Dynamic Range Image Conversion"; Japanese Journal of Dermatology; vol. 123, No. 2, pp. 121-131; Feb. 2013 and English abstract of the same (12 pages).
Office Action dated Aug. 16, 2016 for Japanese Patent Application No. 2014-220046 and English translation of the same. (5 pages).
PC Fan; "The trouble on PC should be solved by applications; It kicks off softly!"; Jun. 2011; vol. 18th; No. 6; p. 136-137 (Partial English Translation).

\* cited by examiner

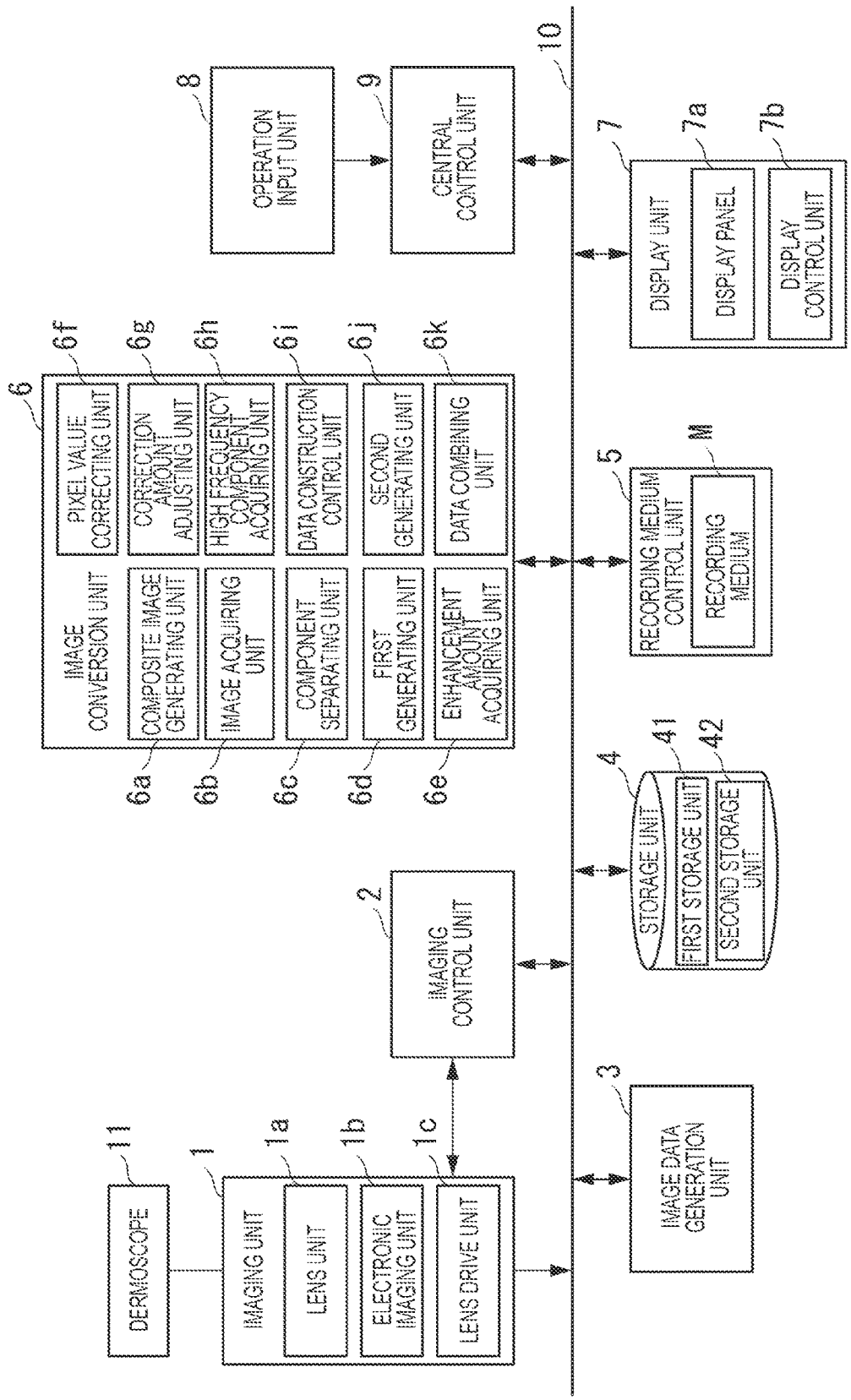

FIG. 9

MEDICAL SKIN EXAMINATION DEVICE AND METHOD FOR ENHANCING AND DISPLAYING LESION IN PHOTOGRAPHED IMAGE

BACKGROUND OF THE INVENTION

1. Field of the Invention

The present invention relates to a medical device, particularly, a medical skin examination device for dermoscopy.

2. Description of the Related Art

The dermoscopy holds a prominent position in diagnosing pigmented skin lesions in the dermatological field. The dermoscopy is an examination method for observing color distribution and structures in epidermis and a dermis superficial layer, in which an area of a lesion is observed by using a dermoscope. In a related art, proposed is an image processing algorithm whereby a skin abnormality can be clearly grasped by applying image processing to an image captured by using the dermoscope (for example, U.S. Pat. No. 7,689, 016).

Meanwhile, in the case of obtaining findings related to a dermoscopy structure of a skin lesion, such as skin cancer or malignant tumors, from a dermoscopy image, it is quite difficult for a doctor having insufficient diagnosis skill to correctly comprehend a larger number of the structures from the dermoscopy image and grasp them as the findings although using technique disclosed in U.S. Pat. No. 7,689, 016. Therefore, providing a medical skin examination device whereby findings from the dermoscopy image can be easily obtained without depending on the doctor's diagnosis skill has been desired.

Considering such a situation, an object of the present invention is to provide a medical skin examination device whereby findings from the dermoscopy image can be easily obtained without depending on the doctor's diagnosis skill

SUMMARY OF THE INVENTION

According to a first aspect of the present invention, a medical skin examination device configured to diagnose a skin lesion, including: a first storage unit configured to store an original first skin image related to a dermoscopy structure imaged via a dermoscope; an image conversion unit configured to apply High Dynamic Range (HDR) conversion processing to the first skin image and obtain a second skin image in which the dermoscopy structure is made clear and salient; a second storage unit configured to store the second skin image; and a display control unit configured to execute control so as to display at least one of the first skin image and the second skin image.

According to a second aspect of the present invention, a medical skin examination device configured to diagnose a skin lesion, including: a first storage unit configured to store an original first skin image related to a dermoscopy structure imaged via a dermoscope; an image conversion unit configured to apply image enhancement conversion processing to the first skin image and obtain a second skin image in which the dermoscopy structure is made clear and salient; a second storage unit configured to store the second skin image; and a display control unit configured to execute control so as to display at least one of the first skin image and the second skin image, wherein the image conversion unit applies the image enhancement conversion processing to one piece of the first skin image and obtains the second skin image in which the dermoscopy structure is made clear and salient.

According to a third aspect of the present invention, a method of examining a skin lesion, including the steps of: first storing an original first skin image related to a dermoscopy structure imaged via a dermoscope; applying High Dynamic Range (HDR) conversion processing to the first skin image and obtaining a second skin image in which the dermoscopy structure is made clear and salient; secondly storing the second skin image; and executing control so as to display at least one of the first skin image and the second skin image.

According to a fourth aspect of the present invention, a non-transitory computer-readable storage medium storing a program to examine a skin lesion, configured to execute: first storing an original first skin image related to a dermoscopy structure imaged via a dermoscope; applying High Dynamic Range (HDR) conversion processing to the first skin image and obtaining a second skin image in which the dermoscopy structure is made clear and salient; secondly storing the second skin image; and executing control so as to display at least one of the first skin image and the second skin image.

BRIEF DESCRIPTION OF THE DRAWINGS

FIG. 3 is a block diagram illustrating a schematic configuration of a medical skin examination device according to an embodiment applied with present invention;

FIG. 9 is a diagram displaying progression of lesion in the time series by using the second skin image applied with the High Dynamic Range (HDR) conversion processing as examples of the melanocytic nevi.

DETAILED DESCRIPTION OF THE PREFERRED EMBODIMENTS

An embodiment to implement the present invention (hereinafter referred to as embodiment) will be described in detail with reference to the attached drawings. Note that same elements throughout an entire part of the description for the embodiment are denoted by the same reference numbers or signs.

Figure 1:
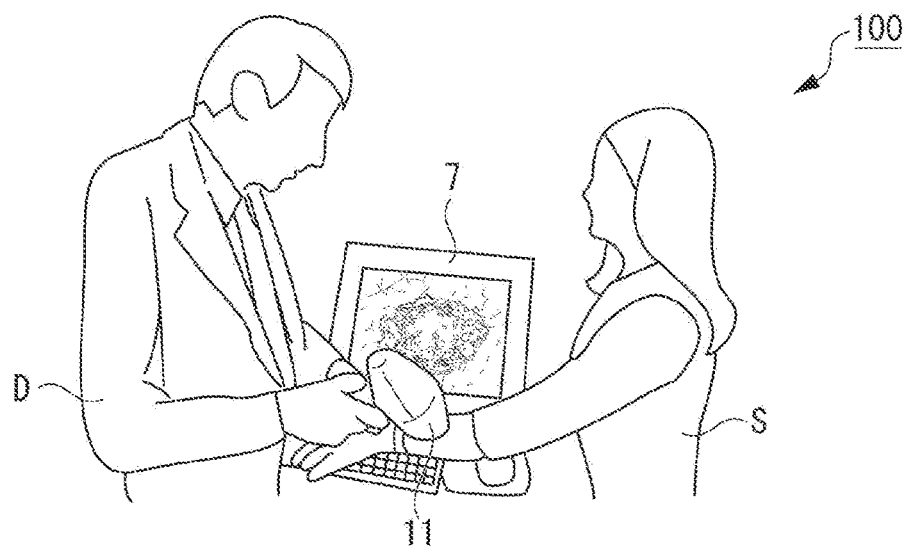
FIG. 1 is a diagram illustrating a state in which a doctor diagnoses an area of a skin lesion (dermoscopy structure) on an arm of a patient by using a contact dermoscope.

FIG. 1 is a diagram illustrating a state in which a doctor diagnoses an area of a skin lesion on an arm of a patient by using a contact dermoscope.

A dermoscope 11 is a magnifier having a light source such as a halogen lamp and a white LED. The area of a lesion of the patient S is applied with gel or the like, and irradiated by the light source while being directly contacted with the dermoscope, and data of an image captured by sight or a digital camera mounted with the dermoscope 11 is digitally converted, and then displayed on a display or the like (a display unit 7 later described) for observation.

Targets of observation utilizing the dermoscopy may include a pigmented skin lesion, such as a melanoma (malignant melanoma), a melanocytic nevus (mole), a basal cell carcinoma, and keratosis seborrheica, an angioma, a hematoma, etc.

As an example, a melanoma or a mole which is the melanocyte lesion is diagnosed. A doctor D diagnoses the area of the lesion on the arm of the patient S by using the dermoscope 11, and observes distribution of melanin pigments. In the case of observing the distribution of melanin pigments, the doctor D observes a net-like pigment deposition pattern called a pigment network. The pigment network is classified into a typical pigment network having a regular mesh that can be observed in a mole and an atypical pigment network having an irregular mesh that can be observed in a melanoma. The typical pigment network has a uniform color tone and tends to be faint and blurred at a periphery thereof, and further includes the mesh formed fine and regularly. On the other hand, the atypical pigment network has the mesh thick and irregular, and the color tone is dark up to the periphery.

Figure 2A:
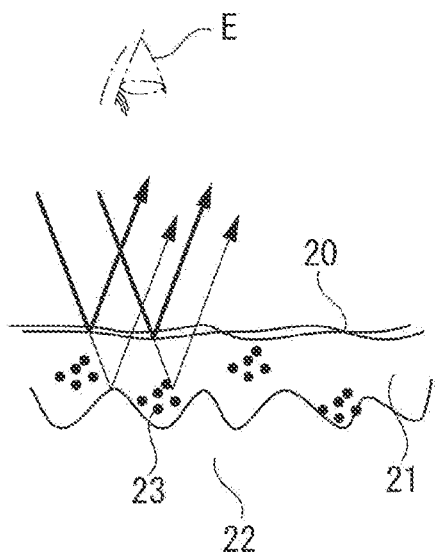
FIG. 2A is a diagram illustrating an optical principle in the case of observing an area of a skin lesion (dermoscopy structure) by using the contact dermoscope, which is the case where observation is executed directly with naked eyes.
Figure 2B:
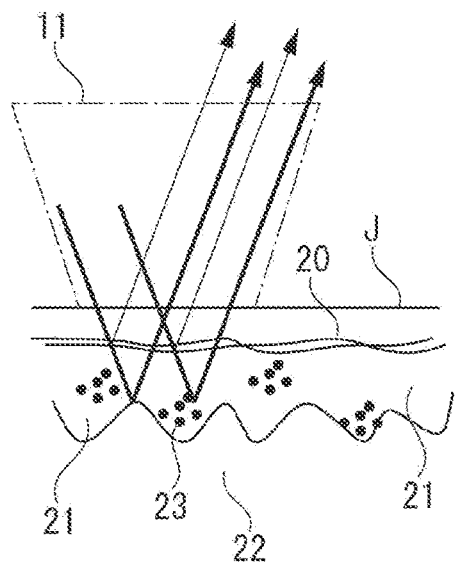
FIG. 2B is a diagram illustrating an optical principle in the case of observing the area of the skin lesion (dermoscopy structure) by using the contact dermoscope, which is a case where observation is executed by using the dermoscope.

As illustrated in FIG. 2A, in the case of executing observation with a naked eye E or a loupe, diffuse reflection occurs in a dead skin cell 20, and therefore, unevenness on a surface can be observed, but internal pigment distribution and the color tone can be observed only with a blurred view. On the other hand, as illustrated in FIG. 2B, in the case of applying gel J for echography on the area of the lesion or suppressing reflection by a conversion filter or the like by using the dermoscope 11, the unevenness on the surface disappears and the diffuse reflection is eliminated. Therefore, the pigment distribution can be observed from the inside of epidermis 21 to a superficial layer of dermis 22. As a result, melanin pigments 23 not clearly viewed by the naked eye E can be clearly observed by utilizing the dermoscope 11.

In contrast, a clearer image can be provided by applying the present invention.

FIG. 3 is a block diagram illustrating a schematic configuration of a medical skin examination device according to the present embodiment. As illustrated in FIG. 3, a medical skin examination device 100 according to the embodiment includes an imaging unit 1, an imaging control unit 2, an image data generation unit 3, a storage unit 4, a recording medium control unit 5, an image conversion unit 6, a display unit 7, an operation input unit 8, and a central control unit 9. Further, the imaging unit 1, imaging control unit 2, image data generation unit 3, storage unit 4, recording medium control unit 5, image conversion unit 6, display unit 7, and central control unit 9 are mutually connected via a bus line 10.

The imaging unit 1 images a predetermined object and generates a frame image. More specifically, the imaging unit 1 includes a lens unit 1a, an electronic imaging unit 1b, and a lens drive unit 1c. Note that the dermoscope 11 is mounted on the imaging unit 1.

The lens unit 1a includes, for example, a plurality of lenses such as a zoom lens and a focus lens.

The electronic imaging unit 1b includes an image sensor (imaging device) such as a CCD (Charge Coupled Device) and a CMOS (Complementary Metal-oxide Semiconductor). Further, the electronic imaging unit 1b converts an optical image passing the various kinds of lenses in the lens unit 1a to a two-dimensional image signal. The lens drive unit 1c includes, for example, a zoom drive unit configured to move the zoom lens in an optical axis direction, a focus drive unit configured to move the focus lens in the optical axis direction, and the like although not illustrated. Note that the imaging unit 1 may include a diaphragm (not illustrated) configured to adjust a light amount of the lens unit 1a in addition to the lens unit 1a, electronic imaging unit 1b, and lens drive unit 1c.

The imaging control unit 2 controls object imaging executed by the imaging unit 1. Specifically, the imaging control unit 2 includes a timing generator, a driver, and so on although not illustrated. Further, the imaging control unit 2 scans and drives the electronic imaging unit 1b by the timing generator and the driver, and causes the electronic imaging unit 1b to convert the optical image passing the lens unit 1a to the two-dimensional image signal in a predetermined cycle. Then, the imaging control unit 2 reads out a frame image for each screen from an imaging area of the electronic imaging unit 1b and causes the image data generation unit 3 to output the frame image.

Further the imaging control unit (imaging control means) 2 controls the imaging unit 1 so as to capture, a plurality of times, images having substantially a same composition while varying exposure conditions. Specifically, the imaging control unit 2 controls execution of, so to say, exposure bracket imaging, and sequentially sets the exposure conditions when the object is imaged by the imaging unit 1. In other words, the imaging control unit 2 adjusts shutter speed (exposure time), a signal amplification factor (ISO sensitivity), an aperture value of the diaphragm, etc. of the electronic imaging unit 1b based on a predetermined program diagram. Further, the imaging control unit 2, for example, sets an appropriate exposure as a reference value, and controls the shutter speed, signal amplification factor, aperture value, etc. such that the exposure conditions become overexposure and underexposure based on the reference value. Also, the imaging control unit 2 causes the imaging unit 1 to consecutively capture a plurality of images having substantially the same composition while keeping a focal length in a fixed state. In other words, the imaging control unit 2 causes the imaging unit 1 to consecutively capture the plurality of the images having substantially the same composition while changing luminance in multiple levels.

Meanwhile, the imaging control unit 2 may be configured to adjust a focusing position of the lens unit 1a by moving the electronic imaging unit 1b in the optical axis direction instead of moving the focus lens of the lens unit 1a.

Further, the imaging control unit 2 may be configured to control adjustment of the conditions such as AF (automatic focus processing), AE (automatic exposure processing), and AWB (automatic white balance) at the time of imaging the object.

The image data generation unit 3 executes, for each of RGB color components, suitable gain adjustment with respect to a signal of an analog value of the frame image transmitted from the electronic imaging unit 1*b*, and then samples and holds the signal in a sample-and-hold circuit (not illustrated) to convert the analog signal to digital data by an A/D converter (not illustrated), subsequently executes color process processing including pixel interpolation processing and γ correction processing in a color process circuit (not illustrated), and after that, generates a luminance signal Y and color-difference signals Cb, Cr (YUV data) having digital values.

The luminance signal Y and the color-difference signals Cb, Cr output from the color process circuit are DMA-transferred to the storage unit 4 used as a buffer storage unit via a DMA controller not illustrated.

The storage unit 4 is formed of, for example, a DRAM (Dynamic Random Access Memory) and the like, and temporarily stores the data to be processed by the image conversion unit 6, central control unit 9, and so on. A first storage unit 41 and a second storage unit 42 are allocated in the storage unit 4. The first storage unit 41 stores the original first skin image related to the dermoscopy structure imaged via the dermoscope 11, and the second storage unit 42 stores the second skin image obtained from the image conversion unit 6. The second skin image is applied with the High Dynamic Range (HDR) conversion processing whereby the dermoscopy structure is made clear and salient. The second skin image stored in the second storage unit 42 is stored correlated to the first skin image. The image conversion unit 6 can also execute the High Dynamic Range (HDR) conversion processing by using an image in a past medical chart stored in the first storage unit 41.

Here, the first storage unit 41 stores the original first skin image related to the dermoscopy structure imaged via the dermoscope 11, and this image is a composite image obtained through processing in steps from S1 to S3 in a later-described flowchart in FIG. 4, namely, the above-described composition processing. However, in the case of using the image related to the dermoscopy structure in the past medical chart, the past image may be stored in the first storage unit 41 and applied with image enhancement processing in step S4 in FIG. 4. In this case, the image related to the dermoscopy structure in the past is deemed as the original first skin image. After that, the image conversion unit 6 applies the High Dynamic Range (HDR) conversion processing to the image, and the second skin image is obtained. Note that the term High Dynamic Range (HDR) conversion processing is applied to at least one of or both of the composition processing in step S3 and the enhancement processing in step S4 in FIG. 4.

The recording medium control unit 5 includes a recording medium M in a detachable manner, and controls data reading from the attached recording medium M or data writing in the recording medium M. Specifically, the recording medium control unit 5 reads out, from the recording medium M, the image data of a still image encoded in accordance with a predetermined coding system (e.g., JPEG format, motion JPEG format, MPEG format, etc.) and image data of a moving image including a plurality of image frames, and transfers the readout image data to the image conversion unit 6.

Note that the recording medium M is formed of, for example, a non-volatile memory (flash memory) or the like, but this is only an example and not limited thereto and can be suitably and optionally changed.

The image conversion unit 6 includes a composite image generating unit 6*a*, an image acquiring unit 6*b*, a component separating unit 6*c*, a first generating unit (first generating means) 6*d*, an enhancement amount acquiring unit 6*e*, a pixel value correcting unit (correcting means) 6*f*, a correction amount adjusting unit 6*g*, a high-frequency component acquiring unit 6*h*, a data construction control unit (controlling means) 6*i*, a second generating unit 6*j*, and a data combining unit 6*k*. The respective units in the image conversion unit 6 are, for example, formed of predetermined logic circuits but the configurations are merely examples and not limited thereto.

The composite image generating unit 6*a* generates the composite image obtained by expanding a dynamic range. Specifically, the composite image generating unit 6*a* executes pixel addition to a plurality of image data obtained by the control of the imaging control unit 2, and executes control so as to generate the image data obtained by expanding the dynamic range. More specifically, the composite image generating unit 6*a* obtains, from the storage unit 4, the image data having the substantially same composition and imaged a plurality of times while varying the exposure conditions (e.g., appropriate exposure, underexposure, overexposure, etc.), and then generates the image data of the composite image (YUV data) having the expanded dynamic range obtained by adding luminance components of corresponding pixels in these image data. Note that the processing of generating the image data of the composite image is a known technology, and therefore, a detailed description therefor will be omitted here.

The image acquiring unit 6*b* acquires an image to be processed by the image enhancement processing (described later). Specifically, the image acquiring unit (acquiring means) 6*b* acquires image data of the image to be processed. More specifically, the image acquiring unit 6*b* acquires the image data of the composite image generated by the composite image generating unit 6*a*. For example, the image acquiring unit 6*b* acquires a copy of the image data (YUV data) of the composite image generated by the composite image generating unit 6*a* from the storage unit 4, or acquires a copy of the image data of the composite image stored in the recording medium M. Meanwhile, respective processing by the image conversion unit 6 later described may be directly applied to the image data of the composite image, or may be applied a reduced image data obtained by reducing the image data of the composite image at a predetermined reduction ratio (e.g., VGA size or the like) depending on necessity.

The component separating unit 6*c* separates an image component to be processed. Specifically, the component separating unit (separating means) 6*c* separates image data of a predetermined color space acquired by the image acquiring unit 6*b* into respective components. More specifically, the component separating unit 6*c* separates the image data of the composite image acquired by the image acquiring unit 6*b* into, for example, a luminance component (luminance value) Y_hdr and color difference components U_hdr, V_hdr, and then outputs the components.

Meanwhile, it has been described that the image data is separated into the luminance component (intensity value) Y_hdr and the color difference components U_hdr, V_hdr, but this is merely an example and not limited thereto, and therefore, may be suitably and optionally changed. For example, the image data may be separated into respective color components of an RGB color space or an LAB color space.

The first generating unit 6*d* generates multiple levels of pixel values smoothed at multiple levels of resolutions.

Specifically, the first generating unit (first generating means) 6*d* repeatedly applies smoothing processing and resolution conversion processing to the pixel value of the image data of the image to be processed acquired by the image acquiring unit 6b, and generates the multiple levels of the pixel value smoothed at each of the multiple levels of resolutions. More specifically, the first generating unit 6d repeatedly applies, by using a Gaussian pyramid, the smoothing processing and the resolution conversion processing to the luminance component (luminance value) Y_hdr of the composite image acquired by the image acquiring unit 6b and separated by the component separating unit 6c, and generates the multiple levels of the pixel values smoothed at each of the multiple-levels of resolutions.

For instance, the first generating unit 6d sequentially repeats the smoothing processing and the resolution reduction processing to the luminance component Y_hdr of the composite image, and generates a Gaussian pyramid Y_G_pyramid [n] having n levels of the luminance components Y_hdr. In other words, according to the Gaussian pyramid, the higher the level of the pyramid is (the larger the value is), the less smoothing is applied, thereby representing big-picture contrast of the luminance components Y_hdr. Subsequently, the first generating unit 6d applies smoothing to each level of the n-level Gaussian pyramid Y_G_pyramid [n] of the luminance components Y_hdr by using an edge preserving filter, and generates a smoothed Gaussian pyramid Y_G_pyramid_lpf[n] having the n levels. Here, by using the edge preserving filter, only smaller amplitude is smoothed.

In this manner, details having frequencies of a lower frequency band is enhanced through pixel value correction (later described) by the pixel value correcting unit 6f on a flat portion, thereby achieving to represent dynamic enhanced contrast, such as producing 3D appearance for a big cloud. Further, even in the case where the Gaussian pyramid has the small number of n levels, the details having the frequencies of the low frequency band can be easily enhanced. Note that processing of generating the Gaussian pyramid is a known technology, and therefore, a detailed description therefore will be omitted here.

The enhancement amount acquiring unit 6e acquires an enhancement amount for the pixel value at each of the multiple levels of resolutions. Specifically, the enhancement amount acquiring unit (second acquiring means) 6e acquires the enhancement value for the pixel value in each level based on a difference between a pixel value of the image data of the image to be processed captured by the image acquiring unit 6b and a pixel value in each level generated by the first generating unit 6d. More specifically, the enhancement amount acquiring unit 6e expands and then resizes, to an original size, each level of the n-level smoothed Gaussian pyramid Y_G_pyramid_lpf[n] of the luminance components Y_hdr to generate a resized smoothed Gaussian pyramid Y_G_pyramid_lpf_rsz[n] having the n levels. Further, the enhancement amount acquiring unit 6e normalizes, to values in a range from "0" to "1", the luminance component Y_hdr in each pixel of the composite image to be processed and the luminance component in each pixel of the n-level resized smoothed Gaussian pyramid Y_G_pyramid_lpf_rsz[n] of the luminance components Y_hdr, and acquires the enhancement amount for the luminance component Y_hdr in each level based on the difference between the normalized values.

The pixel value correcting unit 6f corrects the pixel value at each of the multiple levels of resolutions. Specifically, the pixel value correcting unit (correcting means) 6f corrects the pixel value of the image data acquired for each level based on the difference between the pixel value of the image data of the image to be processed acquired by the image acquiring unit 6b and the pixel value generated by the first generating unit 6d for each level.

More specifically, the pixel value correcting unit 6f executes, for example, correction to enhance the pixel value of the luminance component Y_hdr per resolution by the enhancement amount for each level of the multiple levels of the luminance components Y_hdr acquired by the enhancement amount acquiring unit 6e, and generates n levels of enhanced luminance components Y_detail_up[n] in which the details of the luminance components Y are enhanced. As a result of this, for example, in the case of using a lower level, which has a high resolution and a low smoothing level, of the n-level resized smoothed Gaussian pyramid Y_G_pyramid_lpf_rsz[n], the pixel value correcting unit 6f enhances details having frequencies of the high-frequency band. In contrast, in the case of using a high level of the same pyramid having a low resolution and a high smoothing level, the pixel value correcting unit 6f enhances details having frequencies of a broad frequency band from high to low frequency bands.

The correction amount adjusting unit 6g adjusts the correction amount of the pixel value at each of the multiple levels of resolutions. Specifically, the correction amount adjusting unit (adjusting means) 6g adjusts the correction value of the pixel value at each of the multiple levels of resolutions corrected by the pixel value correcting unit 6f. More specifically, the correction amount adjusting unit 6g adjusts the enhancement level in each level of the multiple levels of the luminance components Y_hdr acquired by the enhancement amount acquiring unit 6e (see FIG. 6). Here, adjustment of the correction value of the pixel value may be executed, for example, at a correction level specified from among a plurality of preset specified correction levels based on predetermined operation by a user at the operation input unit 8, or may be executed at a correction level optionally specified by the user.

Figure 6:
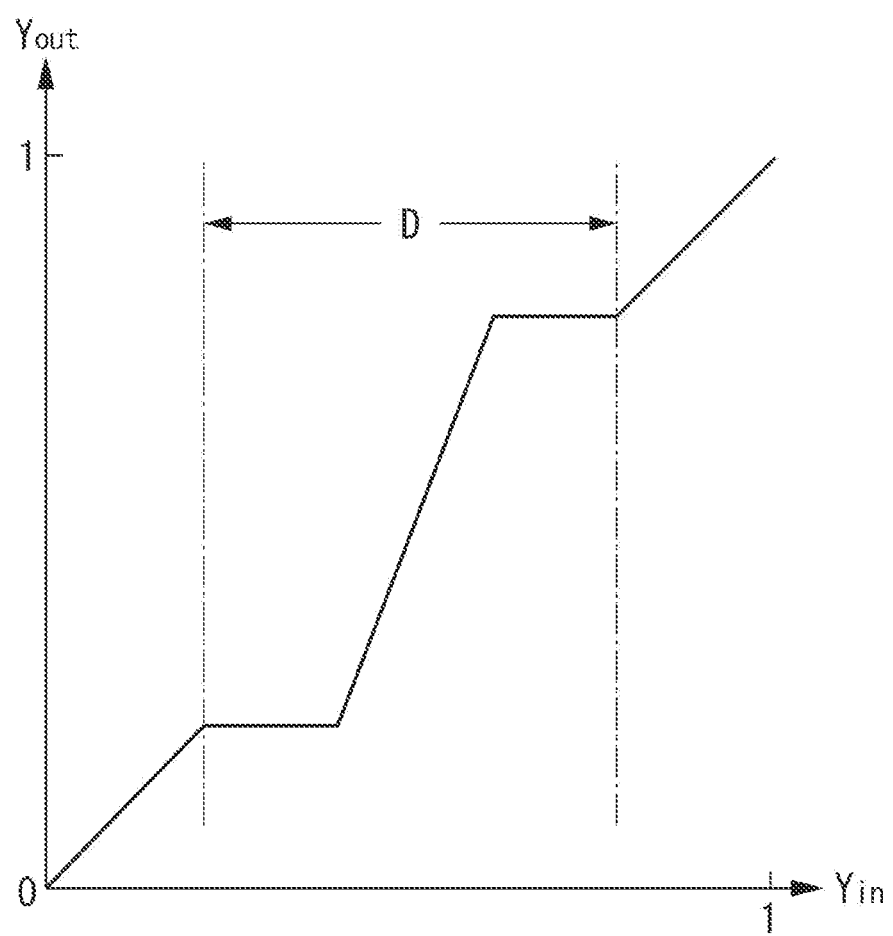
FIG. 6 is a diagram for describing adjustment of a correction amount of a pixel value in the image enhancement processing in FIG. 5.

For example, FIG. 6 is a diagram illustrating a correlation relation between a luminance value Yin of an input image and a luminance value Yout of an output image after enhancement. In FIG. 6, a reference position (e.g., center) of a detail setting width D is determined by a value of the luminance component in each pixel of the n-level resized smoothed Gaussian pyramid Y_G_pyramid_lpf_rsz[n]. Further, the more the correction amount adjusting unit 6g increases the enhancement level (gain level), the smaller the difference between the luminance component Y_hdr in each pixel of the composite image to be processed and the luminance component in each pixel of the n-level resized smoothed Gaussian pyramid Y_G_pyramid_lpf_rsz[n] of the luminance components Y_hdr is. As a result, the details having smaller amplitude (portion not including the high-frequency component) are more enhanced among the luminance components Y, and the details can be fully represented. On the other hand, unnecessary enhancement can be suppressed because the details having large amplitude (portion including the high-frequency component) among the luminance components Y originally are not enhanced.

Meanwhile, when the detail setting width D is set wide, high enhancement can be effected to the high-frequency component as well, but overshoot or undershoot may be caused at a portion having a large amount of contrast.

The high-frequency component acquiring unit 6h acquires a high-frequency component with respect to the pixel value in each level of the multiple levels. Specifically, the high-frequency component acquiring unit (third acquiring means) 6h acquires the high-frequency components at the multiple levels of resolutions with respect to the luminance component Y in each level corrected by the pixel value correcting unit 6f. More specifically, the high-frequency component acquiring unit 6h acquires, by using a Laplacian pyramid, the high-frequency component with respect to the luminance component Y in each level of the multiple levels.

For example, the high-frequency component acquiring unit 6h generates the Laplacian pyramid having n levels with respect to each of the n levels of the enhanced luminance components Y_detail_up[n] generated by the pixel value correcting unit 6f. In other words, the high-frequency component acquiring unit 6h generates the Laplacian pyramid Y_L_pyramid_detail_up[n][n] having n levels×n groups, in which each of the n levels of the enhanced luminance components Y_detail_up[n] is deemed as a group. Note that the process of generating the Laplacian pyramid is a known technology whereby a Gaussian pyramid is generated for each level of the n levels of the enhanced luminance components Y_detail_up[n], and acquires a difference between the adjacent levels. Therefore, a detailed description therefor will be omitted here.

The data construction control unit 6i constructs image data having the enhanced pixel value. Specifically, the image data in each level having the pixel value corrected by the pixel value correcting unit 6f has a high-frequency component. The data construction control unit 6i executes control so as to construct image data having the enhanced pixel value of the acquired image data by using the high-frequency component corresponding to each level of the resolutions. More specifically, the data construction control unit 6i identifies, among the high-frequency components of the multiple levels acquired by the high-frequency component acquiring unit 6h, the high-frequency component corresponding to the resolution at which the pixel value is corrected by the pixel value correcting unit 6f, and executes control so as to construct the image data having the enhanced pixel value.

For example, the data construction control unit 6i selects a hierarchical image (luminance component Y) from each level of each of the groups in the Laplacian pyramid Y_L_pyramid_detail_up[n][n] including the n levels×n groups acquired by the high-frequency component acquiring unit 6h, and generates a final Laplacian pyramid Y_L_pyramid_final[n] having n levels. Here, the selecting method is to select a hierarchical image of a level having the same number as a number of each group. For example, the data construction control unit 6i selects, from a group 2 Y_L_pyramid_detail_up[n][2], the hierarchical image Y_L_pyramid_detail_up[2][2] in the second level. Finally, the data construction control unit 6i acquires a copy of the hierarchical image in the $n^{th}$ level of the n-level Gaussian pyramid Y_G_pyramid[n], and incorporates the copy to the highest level of the pyramid to generate the n-level final Laplacian pyramid Y_L_pyramid_final[n].

By this, a lower level layer of the n-level final Laplacian pyramid Y_L_pyramid_final[n] stores a detail component having a frequency of the high-frequency band and enhanced by using the lower level layer of the n-level resized smoothed Gaussian pyramid Y_G_pyramid_lpf_rsz [n] through correction of the pixel value executed by the pixel value correcting unit 6f. Further, an intermediate level layer thereof stores a detail component obtained by extracting only a portion corresponding to the detail component having a frequency of an intermediate frequency band out of the detail components enhanced by using the intermediate level layer of the n-level resized smoothed Gaussian pyramid Y_G_pyramid_lpf_rsz[n] and having frequencies from the intermediate to high-frequency bands. Furthermore, a higher level layer thereof stores a detail component obtained by extracting only a portion corresponding to the detail component having a frequency of the low frequency band out of the detailed components enhanced by using the higher level layer of the n-level resized smoothed Gaussian pyramid Y_G_pyramid_lpf_rsz[n] and having frequencies from the low to high-frequency bands. In other words, the n-level final Laplacian pyramid Y_L_pyramid_final[n] stores the detail components enhanced through correction of the pixel values executed by the pixel value correcting unit 6f and having the frequencies of a variety of frequency bands without having the frequency bands overlapped.

Further, the data construction control unit 6i reconstructs the n-level final Laplacian pyramid Y_L_pyramid_final[n], and generates a luminance component Y_final (luminance image data). For example, the data construction control unit 6i reconstructs the final Laplacian pyramid Y_L_pyramid_final[n] by using a generally used technique in which procedures of "expanding" and "adding" are repeatedly executed for the hierarchical images from a high level of the pyramid, and finalizes the luminance component Y_final.

The second generating unit 6j generates color difference image data having a color difference component enhanced. Specifically, the second generating unit (second generating means) 6j generates the color difference image data in which the color difference components U_hdr, V_hdr separated by the component separating unit 6c are enhanced based on an enhancement degree of the luminance value in the image data constructed by the data construction control unit 6i. More specifically, the second generating unit 6j amplifies, for example, values of the color difference components U_hdr, V_hdr at degree substantially equal to the enhancement amount of the luminance component Y_hdr acquired by the enhancement amount acquiring unit 6e, and finalizes the color difference components U_final, V_final (color difference image data) (not illustrated).

Here, the enhancement amount of the luminance component Y_hdr may be the enhancement amount corresponding to any level of the enhancement amounts out of the luminance components Y_hdr of the respective levels of the multiple levels, or may be the enhancement amount calculated by executing a predetermined operation based on the enhancement amounts corresponding to the multiple levels.

The data combining unit 6k combines the luminance image data with the color difference image data. Specifically, the data combining unit (combining means) 6k combines the luminance component Y_final constructed by the data construction control unit 6i with the color difference components U_final, V_final generated by the second generating unit 6j, and generates image data of an image-processed image HDR_final.

The display unit 7 includes a display panel 7a and a display control unit 7b. The display panel 7a displays an image inside a display screen. Further, the display panel 7a may include, for example, a liquid crystal display panel, an organic EL display panel, etc., but not limited thereto.

The display control unit 7b reads out the image data for display temporarily stored in the storage unit 4, and executes control so as to display a predetermined image on the display screen of the display panel 7a based on the image data having a predetermined size decoded by the image conversion unit 6. More specifically, the display control unit 7b includes a VRAM (Video Random Access Memory), a VRAM controller, a digital video encoder, and so on (all not illustrated). Further, the digital video encoder reads out a luminance signal Y and color difference signals Cb, Cr decoded by the image conversion unit 6 and stored in the VRAM from the VRAM via a VRAM controller at a predetermined reproduction frame rate (e.g., 30 fps), and generates a video signal based on these data, and then outputs the video signal to the display panel 7a.

For example, the display control unit 7b displays a live view image G on the display panel 7a while sequentially updating, at the predetermined frame rate, a plurality of frame images generated by object imaging by the imaging unit 1 and the imaging control unit 2 in a still image imaging mode or a moving image imaging mode. Further, the display control unit 7b displays an image recorded as a still image (REC view image) on display panel 7a or an image recorded as a moving image on the display panel 7a.

Figure 8:
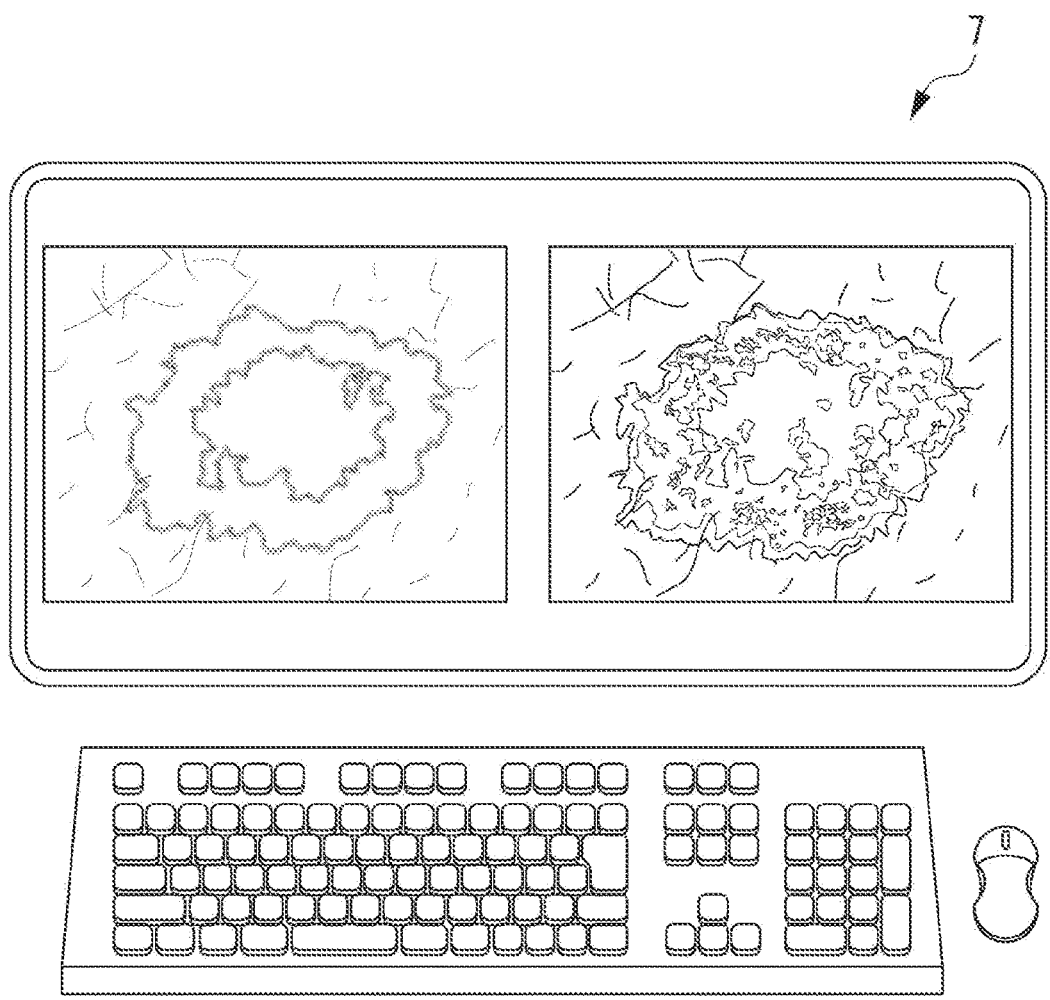
FIG. 8 is a diagram displaying, in parallel, an original first skin image related to a dermoscopy structure imaged via a dermoscope and a second skin image applied with High Dynamic Range (HDR) conversion processing as examples of melanocytic nevi.

Additionally, for example, the display control unit 7b executes control so as to display at least one of the first skin image and the second skin image or display both of the images in parallel in the case of displaying both images as illustrated in an exemplary screen configuration in FIG. 8. Furthermore, for example, the display control unit 7b executes control such that the first skin image and/or the second skin image are displayed in the time series in accordance with progression of a lesion at a dermoscopy structure as illustrated in an exemplary screen configuration in FIG. 9.

The operation input unit 8 is provided to execute the predetermined operation for the medical skin examination device 100. More specifically, the operation input unit 8 includes operating units, such as the shutter button associated with an object imaging command, a selection determining button related to a selection command for selecting an imaging mode or function, and a zoom button related to an adjustment command of a zooming amount (all not illustrated), and outputs a predetermined operation signal to the central control unit 9 in accordance with the operation at the respective buttons of the operating units.

The central control unit 9 is provided to control the respective units of the medical skin examination device 100. More specifically, the central control unit 9 includes a CPU (Central Processing Unit) or the like although not illustrated, and executes various kinds of control operation in accordance with various kinds of programs (not illustrated) for the medical skin examination device 100.

<Imaging Processing>

Next, operation of the medical skin examination device 100 will be described with reference to FIGS. 4 to 9. FIG. 4 is a flow chart illustrating exemplary operation related to the imaging processing.

In the case where an enhanced image capturing mode is selected from among a plurality of operation modes displayed on a menu screen based on the user's predetermined operation to the selection determining button at the operation input unit 8, the imaging processing is executed by the respective units of the medical skin examination device 100 under the control of the central control unit 9.

Figure 4:
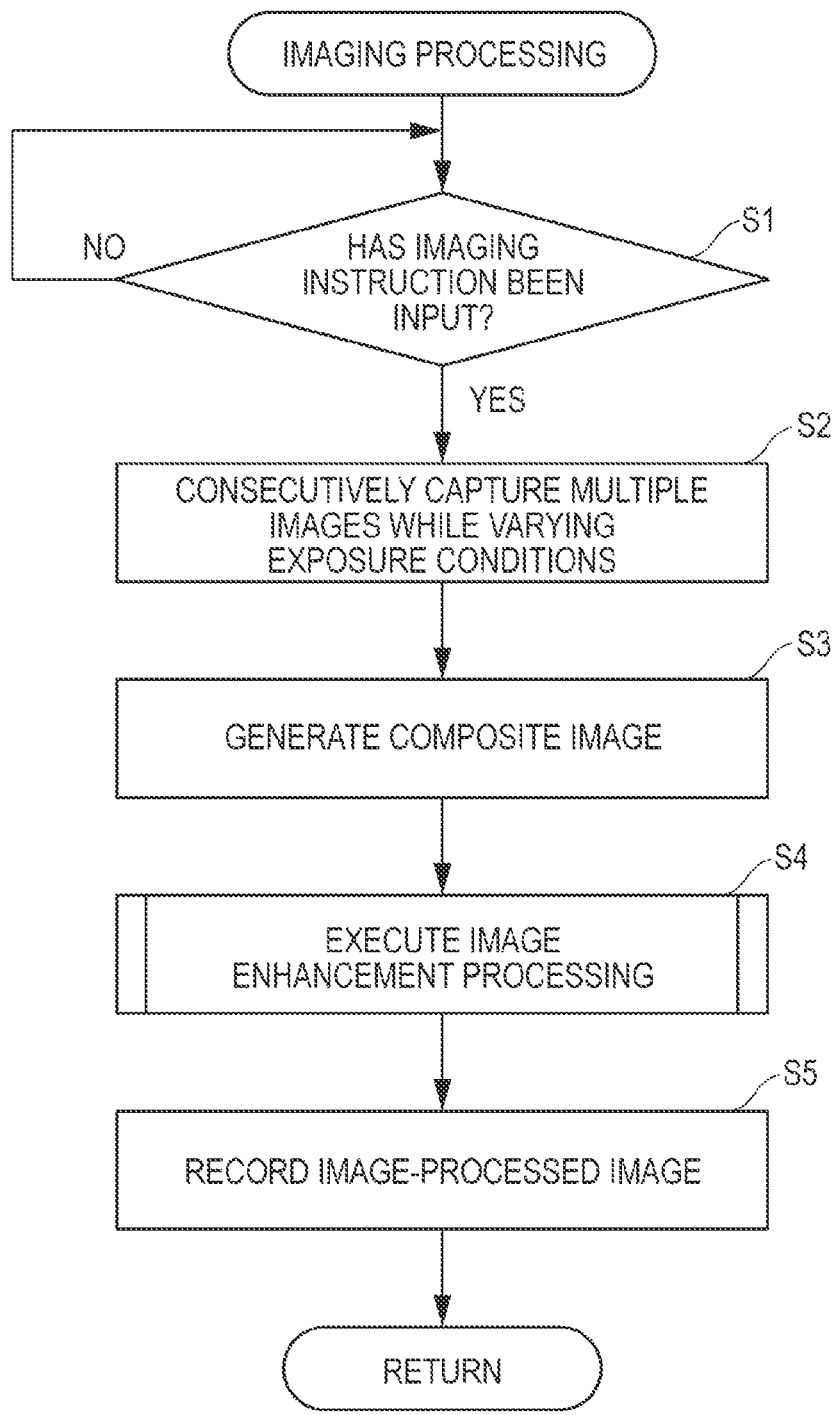
FIG. 4 is a flowchart illustrating exemplary operation related to imaging processing by the medical skin examination device in FIG. 3.

As illustrated in FIG. 4, the CPU at the central control unit 9 first determines whether the imaging instruction is input by the user's predetermined operation to the shutter button at the operation input unit 8 (step S1). The determination on whether the imaging command is input in step S1 is repeatedly executed at a predetermined time interval until it is determined that the imaging command is input (step S1; YES).

In the case of determining in step S1 that imaging command is input (step S1; YES), the CPU of the central control unit 9 outputs an imaging control command to the imaging control unit 2, and the imaging control unit 2 controls the imaging unit 1 so as to consecutively image a plurality of images while varying the exposure conditions (step S2). More specifically, the imaging control unit 2, for example, sets the appropriate exposure as the reference value and controls the shutter speed, signal amplification factor, aperture value, etc. such that the exposure conditions become underexposure and overexposure based on the reference value, and causes the imaging unit 1 to consecutively image the plurality of images (e.g., three images or the like) having substantially the same composition while keeping the focal length in a fixed state. Then, the image data generation unit 3 generates the image data of each of the images consecutively imaged, and outputs the image data to the storage unit 4. In the case of using a past skin image already existing, the processing in steps S1 to S3 can be omitted.

Next, the composite image generating unit 6a of image conversion unit 6 obtains, from the storage unit 4, the image data of each of the images consecutively imaged, and generates the image data (YUV data) of the composite image having the dynamic range expanded by adding the luminance components of the corresponding pixels in these image data (step S3).

Subsequently, the image conversion unit 6 executes the image enhancement processing whereby the details and the contrast of the composite image are enhanced (see FIG. 5) (step S4).

<Image Enhancement Processing>

Figure 5:
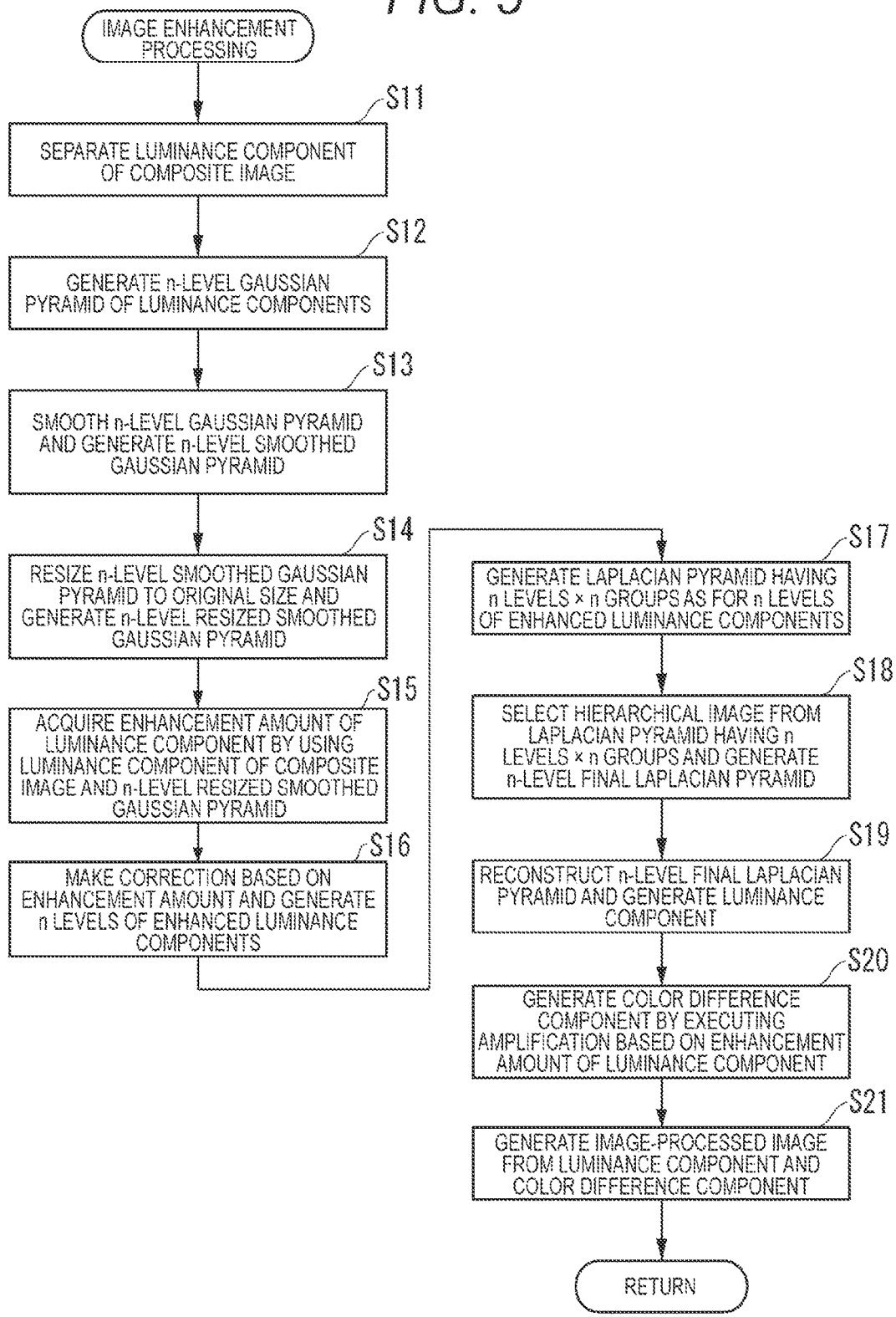
FIG. 5 is a flowchart illustrating exemplary operation related to image enhancement processing in the medical skin examination device in FIG. 3.

The image enhancement processing will be described below with reference to FIG. 5. FIG. 5 is a flowchart illustrating exemplary operation related to the image enhancement processing. As illustrated in FIG. 5, the image acquiring unit 6b of the image conversion unit 6 first acquires the copy of the image data of the composite image generated by the composite image generating unit 6a, and then the component separating unit 6c separates the image data of the composite image into the luminance component (luminance value) Y_hdr and the color difference components U_hdr, V_hdr (step S11). Next, the first generating unit 6d sequentially repeats the smoothing processing and the resolution reduction processing to the luminance component Y_hdr of the composite image, and generates the n-level Gaussian pyramid Y_G_pyramid[n] of the luminance components Y_hdr (step S12). Subsequently, the first generating unit 6d applies the smoothing process to each level of the n-level Gaussian pyramid Y_G_pyramid[n] of the luminance components Y_hdr, and generates the n-level smoothed Gaussian pyramid Y_G_pyramid_lpf[n] (step S13).

Next, the enhancement amount acquiring unit 6e resizes, to the original size, each level of the n-level smoothed Gaussian pyramid Y_G_pyramid_lpf[n] of the luminance component Y_hdr generated by the first generating unit 6d, and generates the n-level resized smoothed Gaussian pyramid Y_G_pyramid_lpf_rsz[n] (step S14).

Subsequently, the enhancement amount acquiring unit 6e normalizes, to the values in the range from "0" to "1", the luminance component Y_hdr in each pixel of the composite image and the luminance component in each pixel of the n-level resized smoothed Gaussian pyramid Y_G_pyramid_lpf_rsz[n] of the luminance components Y_hdr, and acquires the enhancement amount for each level of the luminance component Y_hdr based on the difference between the normalized values (step S15).

Next, the pixel value correcting unit 6f corrects the luminance component Y_hdr of each resolution based on the enhancement amount for each level of the multiple levels of the luminance components Y_hdr acquired by the enhancement amount acquiring unit 6e, and generates the n levels of the enhanced luminance components Y_detail_up[n] (see step S16).

Next, the high-frequency component acquiring unit 6h generates the Laplacian pyramid Y_L_pyramid_detail_up [n][n] having the n levels×n groups, in which the each of the n levels of enhanced luminance components Y_detail_up[n] generated by the pixel value correcting unit 6f is deemed as one group (step S17).

Next, the data construction control unit 6i selects the hierarchical image (luminance component Y) from each level of each of the groups in the Laplacian pyramid Y_L_pyramid_detail_up[n][n] having the n levels×n groups acquired by the high-frequency component acquiring unit 6h, and also generates the n-level final Laplacian pyramid Y_L_pyramid_final[n] by incorporating, into the highest level, the copy of the hierarchical image in the $n^{th}$ level of the n-level Gaussian pyramid Y_G_pyramid[n] (step S18). Subsequently, the data construction control unit 6i reconstructs the n-level final Laplacian pyramid Y_L_pyramid_ final[n] by applying "expanding", "adding", etc. to the hierarchical images sequentially from the high level of the pyramid, and generates the luminance component Y_final (step S19).

Next, the second generating unit 6j amplifies the values of the color difference components U_hdr, V_hdr at the degree substantially equal to the enhancement amount of the luminance component Y_hdr acquired by the enhancement amount acquiring unit 6e, and generates the color difference components U_final, V_final (step S20). Subsequently, the data combining unit 6k combines the luminance component Y_final with the color difference component U_final, V_final, and generates the image data of the image-processed image HDR_final (step S21). Then, the image conversion unit 6 encodes the image data of the image-processed image HDR_final by using the predetermined compression format, and outputs the encoded image data to the storage unit 4.

Back to FIG. 4, the recording medium control unit 5 obtains the encoded image data of the image-processed image HDR_final from the storage unit 4, and has the image data stored in a predetermined storage area of the recording medium M (step S5). Thus, the imaging processing ends.

As described above, according to the medical skin examination device 100 of the present embodiment, the pixel value of the image data acquired in each level is corrected based on the difference between the pixel value (e.g., luminance value) of the image data of the captured image and the pixel values of the multiple levels obtained by smoothing the image data of the captured image at each of the multiple levels of resolutions. The image data having the corrected pixel value in each level includes the high-frequency component. By using the high-frequency component corresponding to each level of the resolution, the image data having the enhanced pixel value of the acquired image data can be constructed.

More specifically, the smoothing processing and the resolution conversion processing are repeatedly applied to the pixel value of the image data of the captured image by using the Gaussian pyramid, thereby achieving to generate the multiple levels of the pixel values smoothed at each of the multiple levels of resolutions. At this point, contrast in the low frequency band can be easily enhanced with the smaller number of levels by smoothing the pixel values at each of the multiple levels of resolutions by using the edge preserving filter.

Further, the enhancement amount of the pixel value in each level is acquired based on the difference between the pixel value of the image data of the captured image and the pixel values of the multiple levels obtained by smoothing the image data of the captured image at each of multiple levels of resolutions. Then, correction to enhance the pixel value of the image data acquired for each level can be executed by the acquired enhancement amount. Furthermore, by using the Laplacian pyramid, the high-frequency components can be obtained at the multiple levels of resolutions with respect to the corrected pixel value in each level, and among the high-frequency components obtained at the multiple levels, the high-frequency component corresponding to the resolution at which the pixel value is corrected is identified, thereby achieving to construct the image data having the enhanced pixel value.

Therefore, by increasing a decomposition level of the frequency related to the image processing for the captured image, the enhancement processing can be applied, more appropriately than the related art, not only to an image area corresponding to the details of the capture image but also to an image area corresponding to the flat portion where contrast difference is hardly noticeable. As a result, the image processing can be executed appropriately regardless degree of contrast difference in the captured image.

Additionally, the correction amount for the smoothed pixel values of the multiple levels can be adjusted. Therefore, the pixel values of the multiple levels can be corrected at correction degree desired by the user, and also enhancement degree for the details and contrast in the image-processed image can be changed.

Moreover, the color difference image data in which the color difference components are enhanced is generated based on the enhancement degree of the luminance value, and the color difference image data is combined with the luminance image data in which the luminance value is enhanced. Therefore, not only the luminance but also color saturation of the captured image can be enhanced, thereby achieving to improve representational power of the details and contrast of the image-processed image.

Furthermore, as the image data of the captured image, the image data obtained by expanding the dynamic range is used. The dynamic range is expanded by executing the pixel addition to the images having substantially same composition and having the luminance varied in the multiple levels. As a result, the image-processed image applied with expansion of the dynamic range can be represented more appropriately. More specifically, the image data obtained by expanding the dynamic range can be generated by executing the pixel addition to the plurality of image data obtained by controlling the imaging unit 1 to capture the images having the substantially same composition the plurality of times while varying the exposure conditions.

Figure 10:
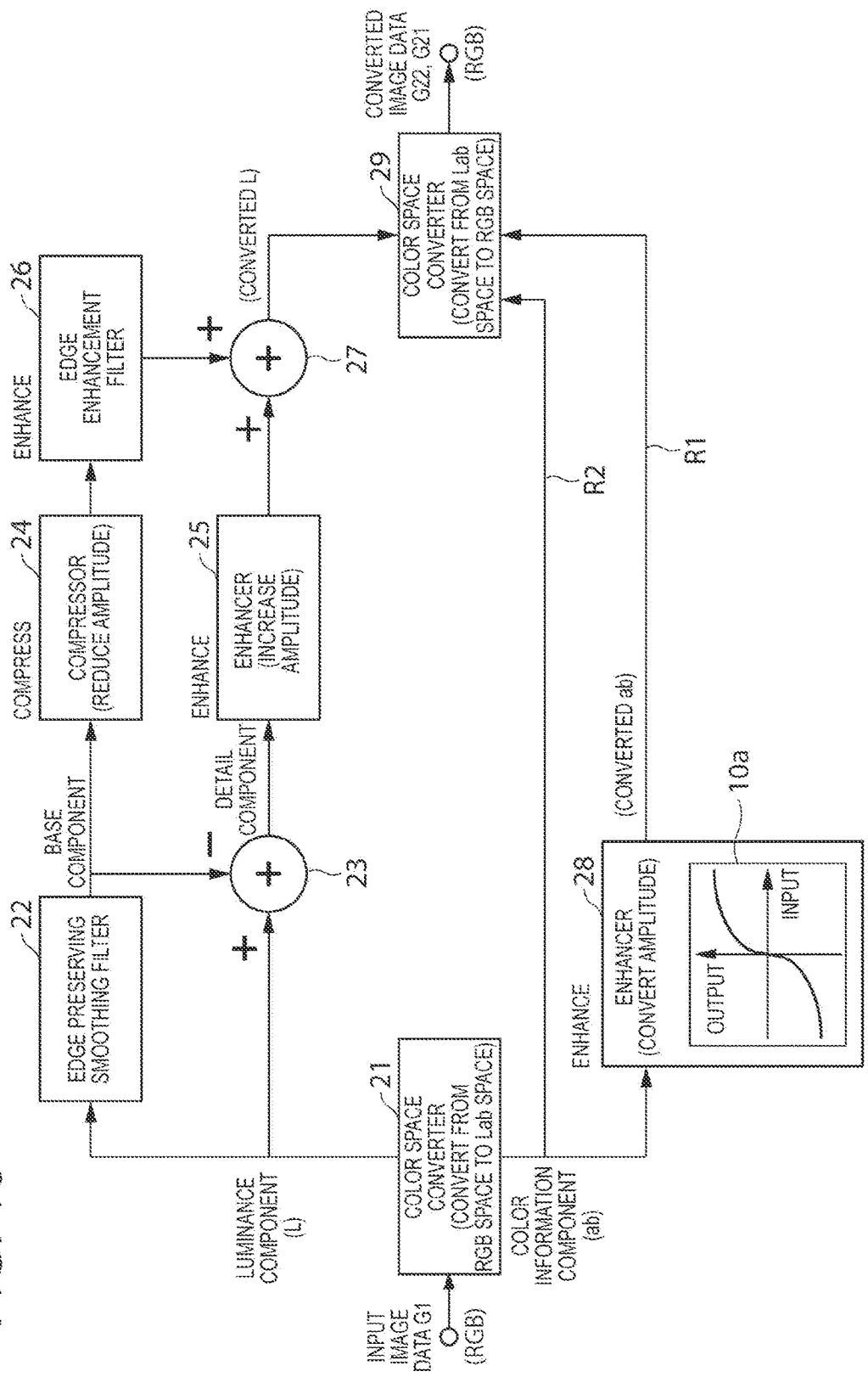
FIG. 10 is a block diagram illustrating a different example of the image enhancement processing in the medical skin examination device in FIG. 3.

Next, a different example of expanding the dynamic range of the image data will be described with reference to FIG. 10. As the image data, the past image data of a patient already stored is used instead of capturing a newly photographed image. Therefore, diagnosis can be performed based the past image data stored with the medical chart without photographing the patient on site. The image data may be JPEG data, but more preferably, RAW data by which the image data having higher image quality and applied with an enhanced conversion can be obtained.

First, an input image G1 which is the past image data is converted from the RGB color space to a CIELab color space by a color space converter 29. An L-axis represents a luminance component, and an a-axis and a b-axis represent color information components.

The luminance component of the input image data G1 is decomposed by a component decomposition filter (e.g., edge preserving smoothing filter 22 such as a bilateral filter and a total variation filter) into a base component (Base Layer) and a detail component (Detail Layer). More specifically, the base component is obtained by passing the luminance component through the component decomposition filter 22, and the detail component is obtained by subtracting the base component from the luminance component by using an adder-subtractor 23.

Next, amplitude of the base component is reduced by a compressor (attenuator) 24, and amplitude of the detail component is increased by an enhancer 25.

Then, the luminance component is converted by adding a signal having an edge enhanced by passing an output signal of the compressor 24 through an edge enhancement filter 26 to an output signal of the enhancer 25 at an adder 27.

The color can be enhanced by increasing the amplitude of the color information components, namely, the a-axis and the b-axis, by use of an enhancer 28 having enhancement property indicated by a reference sign 10a (Route R1).

Here, in the case where nothing is applied to the color information components, more specifically, in the case where the color information components are not passed through the enhancer 28, the image data G22 without change of color tone but applied with the enhanced conversion can be obtained (Route R2).

Finally, a signal of the converted luminance component output from an adder 27 and a signal of the color information component output via the route R1 or R2 are converted at a color space converter 29 from the CIELab color space to the RGB color space, and image data G21 applied with the enhanced conversion can be obtained. The L-axis which is the luminance component of the CIELab color space and the ab axes which are the color information components of the CIELab color space are independent from each other. Therefore, the image data G21 or G22 applied with the enhanced conversion can be obtained by converting the signal of the converted luminance component and the signal of the converted color information component to the RGB color space <Display Processing>

According to the medical skin examination device 100 of the present embodiment, a display mode for a generated image can be changed based on a request from a doctor D who attempts to obtain findings related to a dermoscopy structure of a skin lesion. Specifically, the original first skin image related to the dermoscopy structure imaged via the dermoscope 11 and the second skin image obtained by applying the High Dynamic Range (HDR) conversion processing to the first skin image can be displayed each independently, or displayed together in parallel. Further, the first skin image and/or the second skin image can be displayed in the time series in accordance with progression of a lesion in a dermoscopy structure.

Figure 7:
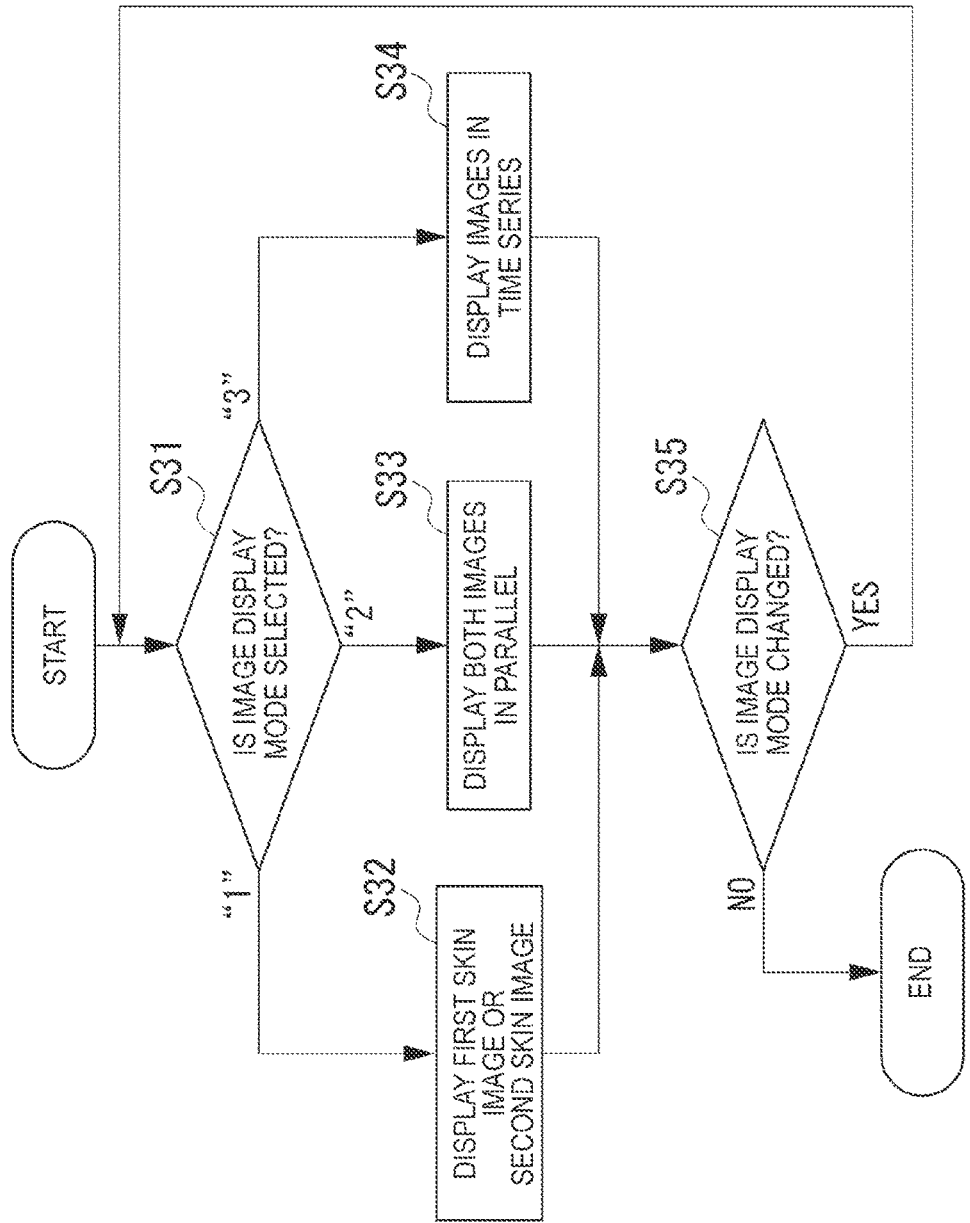
FIG. 7 is a flowchart illustrating exemplary operation related to display processing in the medical skin examination device in FIG. 3.

FIG. 7 is a diagram illustrating an exemplary display control processing. According to FIG. 7, the doctor D attempting to diagnose the lesion selects one of the display modes by operating the operation input unit 8 (step S31). The central control unit 9 reads out this and controls the display control unit 7b. The display control unit 7b refers to either one of or both of the first storage unit 41 and the second storage unit 42, and in the case where a button "1" is pushed (step S31; "1"), for example, the original first skin image related to the dermoscopy structure imaged via the dermoscope 11 or the second sin image obtained by applying the High Dynamic Range (HDR) conversion processing to the first skin image is displayed on the display panel 7a (step S32).

On the other hand, in the case where a button "2" is pushed (step S31; "2"), the display control unit 7b displays both of the above-described first skin image and second skin image in parallel on the display panel 7a (step S33). Here, the second skin image is stored in the storage unit 4, correlated to the first skin image. FIG. 8 is a diagram illustrating an exemplary display example in which the original first skin image related to the dermoscopy structure imaged via the dermoscope 11 and the second skin image obtained by applying the High Dynamic Range (HDR) conversion processing to the first skin image are displayed in parallel as an example of melanocytic nevi. According to the display mode illustrated in FIG. 8, control is made such that the display control unit 7b displays at least one of the first skin image and the second skin image and the display panel 7a displays the two skin images in parallel in the case of displaying both skin images. Therefore, in the latter case, the doctor D attempting to diagnose the lesion can obtain findings by comparing the original first skin image related to the dermoscopy structure imaged via the dermoscope 11 with the second skin image obtained by applying the High Dynamic Range (HDR) conversion processing to the first skin image, and achieves to provide correct diagnosis because the number of graspable findings is increased regardless the doctor's skill.

Figure 9:
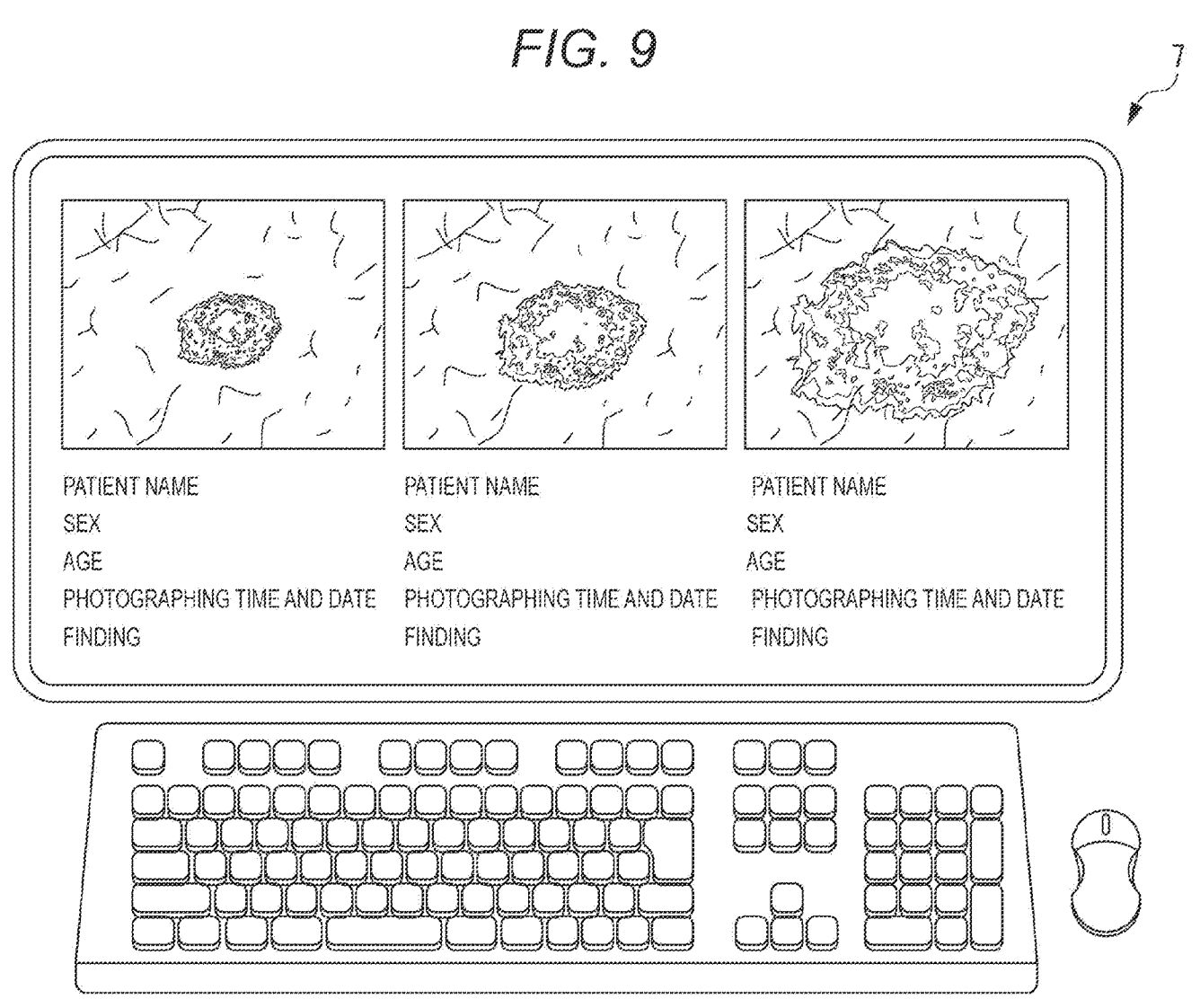

Further, in the case where a button "3" is pushed (step S31; "3"), the display control unit 7b displays the first skin image and/or the second skin image in the time series in accordance with progression of the lesion at the dermoscopy structure (step S34). FIG. 9 is a diagram illustrating a mode of displaying the progression of the lesion in the time series by using the second skin image applied with the High Dynamic Range (HDR) conversion processing as the example of the melanocytic nevi. Therefore, the doctor D attempting to diagnose the lesion can, of course, provide correct diagnosis because the number of graspable findings is increased, but also can check degree of progression of the lesion by the minute. Therefore, the more number of dermoscopy structures can be used to correctly grasp and diagnose the progression of the lesion. In the case of changing selection of the display mode (step S35; "YES"), the processing is returned to step S31 again to select the display mode.

Further, the present invention is not limited to the above-described embodiment and various improvements and modifications of design can be made within the scope without departing from the gist of the present invention. For example, according to the above-described embodiment, the smaller the difference between the luminance component Y_hdr in each pixel of the composite image and the luminance component in each pixel of the n-level resized smoothed Gaussian pyramid Y_G_pyramid_lpf_rsz[n] is, the more the enhancement level is increased. But, this is merely an example and the embodiment is not limited thereto. Therefore, it may be possible that the larger the difference is, the more the enhancement level is increased, for example. In this case, for example, the larger the amplitude of the details is, the more enhancement may be made while the smaller the amplitude of the details is, the less enhancement may be made among the luminance components Y.

Further, the configuration of the medical skin examination device 100 exemplified in the above-described embodiment is an example and not limited thereto. For example, an image may be captured by an external imaging unit and the image enhancement processing may be applied to the image. As for the image control unit, there may be a case of applying a display monitor to which an image to be displayed is transmitted, and further, there may be an applicable case in which the image is transmitted to a printer for printing, or output to a storage medium, such as a memory card, so as to be regenerated and displayed on an external display device.

Additionally, according to the present embodiment, functions as a first storage unit, an image conversion unit, a second storage unit, and a display control unit are implemented by driving the first storage unit 41, image conversion unit 6, second storage unit 42, and the display control unit 7b under control of the central control unit 9. However, not limited thereto, the functions may be implemented by a predetermined program or the like executed by the central control unit 9. More specifically, a program including a first storage routine, an image conversion routine, a second storage routine, and a display control routine is preliminarily stored in a program memory (not illustrated) configured to store the program. Further, the CPU of the central control unit 9 may be configured to function as a storage unit to store the original first image related to the dermoscopy structure imaged via the dermoscope in accordance with the first storage routine. Further, the CPU of the central control unit 9 may be configured to function as a unit to obtain the second skin image in which the dermoscopy structure are made clear and salient by executing the High Dynamic Range (HDR) conversion processing to a piece of the first skin image in accordance with the image conversion routine. Also, the CPU of the central control unit 9 may be configured to function as a unit to store the second skin image in accordance with the second storage routine. Further, the CPU of the central control unit 9 may be configured to function as a unit to display at least one of the first skin image and the second skin image in accordance with the display control routine.

In the same manner, the first generating unit, correction unit, and control unit may be implemented by a predetermined program or the like executed by the CPU of the central control unit 9.

Further, as a computer readable medium that stores a program to execute the above-described respective processing, a ROM, a hard disk, or the like may be applied, and also a non-volatile memory such as a flash memory, or a portable recording medium such as a CD-ROM may be applied. Also, a carrier wave may be applied as a medium to provide program data via a predetermined communication line.

While the embodiment of the present invention has been described, the scope of the present invention is not limited to the above-described embodiment and includes the scope of invention recited in the scope of claims and the scope equivalent thereto.

The invention claimed is:

1. A medical skin examination device configured to diagnose a skin lesion, comprising:
  a first electronic data storage device configured to store an original first skin image related to a dermoscopy structure imaged via a dermoscope;
  a central control unit including a central processing unit configured to apply High Dynamic Range (HDR) conversion processing to the first skin image and obtain a second skin image in which the dermoscopy structure is made clear and salient;
  a second electronic data storage device configured to store the second skin image; and
  a display control unit including a controller and a display configured to execute control so as to display at least one of the first skin image and the second skin image, wherein
  the central processing unit of the central control unit is configured to:
  generate multiple levels of pixel values by repeatedly applying smoothing processing and resolution conversion processing to a pixel value of one piece of the first skin image;
  correct, for each level, a pixel value of the first skin image based on a difference between the pixel value of the first skin image and the generated pixel value in each level; and
  execute control so as to construct the second skin image in which the pixel value of the first skin image is enhanced by utilizing a high-frequency component corresponding to a resolution in each level including the corrected pixel value.

2. The medical skin examination device according to claim 1, wherein the central processing unit applies the High Dynamic Range (HDR) conversion processing to one piece of the first skin image and obtains the second skin image in which the dermoscopy structure is made clear and salient.

3. The medical skin examination device according to claim 2, wherein the first electronic data storage device stores a past image already imaged as the first skin image and stored as a chart, and the central processing unit executes the High Dynamic Range (HDR) conversion processing by using the past image.

4. The medical skin examination device according to claim 1, further including an imaging unit connected to the dermoscope, wherein the first electronic data storage device stores a current image imaged by the imaging unit as the first skin image, and the central processing unit executes the High Dynamic Range (HDR) conversion processing, using the current image.

5. The medical skin examination device according to claim 1, wherein the display control unit executes control so as to display both of the first skin image and the second skin image in parallel.

6. The medical skin examination device according to claim 1, wherein the display control unit executes control so as to display the first skin image and/or the second skin image in the time series in accordance with progression of a lesion of the dermoscopy structure.

7. The medical skin examination device according to claim 1, wherein the second skin image is stored correlated to the first skin image.

8. A medical skin examination device configured to diagnose a skin lesion, comprising:
  a first electronic data storage device configured to store an original first skin image related to a dermoscopy structure imaged via a dermoscope;
  a central control unit including a central processing unit configured to apply image enhancement conversion processing to the first skin image and obtain a second skin image in which the dermoscopy structure is made clear and salient;
  a second electronic data storage device configured to store the second skin image; and
  a display control unit including a controller and a display configured to execute control so as to display at least one of the first skin image and the second skin image;
  wherein the central processing unit of the central control unit is configured to:

apply the image enhancement conversion processing to one piece of the first skin image and obtain the second skin image in which the dermoscopy structure is made clear and salient;
input and separate the first skin image into a luminance component and a color component;
separate the separated luminance component into a base component and a detail component;
compress the base component;
enhance the detail component; and
combine the luminance component having the compressed base component with the luminance component having the enhanced detail component.

9. The medical skin examination device according to claim 8, wherein the image conversion unit further includes a second combination unit configured to combine the separated color component with the luminance component combined at the first combination unit so as to obtain the second skin image.

10. The medical skin examination device according to claim 8, wherein the image conversion unit further includes a second combination unit configured to input the separated color component to a second enhancement unit configured to enhance amplitude, and combine the enhanced color component with the luminance component combined at the first combination unit so as to obtain the second skin image.

11. The medical skin examination device according to claim 10, wherein a first enhancement unit is configured to linearly extend amplitude of an input signal, and the second enhancement unit is configured to non-linearly extend amplitude of an input signal.

12. The medical skin examination device according to claim 8, wherein the first separation unit in the image conversion unit includes a first color space conversion unit configured to convert the input first skin image from an RGB color space to a CIELab color space, and input an L-axis of the CIELab color space to the second separation unit as a luminance component.

13. The medical skin examination device according to claim 8, wherein the second combination unit of the image conversion unit includes a second color space conversion unit configured to execute conversion from a CIELab color space to a RGB color space.

14. A method of examining a skin lesion, comprising the steps of:
first storing an original first skin image related to a dermoscopy structure imaged via a dermoscope;
applying High Dynamic Range (HDR) conversion processing to the first skin image and obtaining a second skin image in which the dermoscopy structure is made clear and salient;
secondly storing the second skin image;
executing control so as to display at least one of the first skin image and the second skin image;
generating multiple levels of pixel values by repeatedly applying smoothing processing and resolution conversion processing to a pixel value of one piece of the first skin image;
correcting, for each level, a pixel value of the first skin image based on a difference between the pixel value of the first skin image and the generated pixel value in each level; and
executing control so as to construct the second skin image in which the pixel value of the first skin image is enhanced by utilizing a high-frequency component corresponding to a resolution in each level including the corrected pixel value.

15. A non-transitory computer-readable storage medium storing a program to examine a skin lesion, configured to execute:
first storing an original first skin image related to a dermoscopy structure imaged via a dermoscope;
applying High Dynamic Range (HDR) conversion processing to the first skin image and obtaining a second skin image in which the dermoscopy structure is made clear and salient;
secondly storing the second skin image;
executing control so as to display at least one of the first skin image and the second skin image;
generating multiple levels of pixel values by repeatedly applying smoothing processing and resolution conversion processing to a pixel value of one piece of the first skin image;
correcting, for each level, a pixel value of the first skin image based on a difference between the pixel value of the first skin image and the generated pixel value in each level; and
executing control so as to construct the second skin image in which the pixel value of the first skin image is enhanced by utilizing a high-frequency component corresponding to a resolution in each level including the corrected pixel value.

* * * * *